United States Patent [19]
Powell et al.

[11] Patent Number: 5,887,591
[45] Date of Patent: Mar. 30, 1999

[54] RESTRAINT AND METHOD FOR THE IMPROVED TREATMENT OF RECALCITRANT PLANTAR FASCIITIS

[76] Inventors: Mark W. Powell, 2363 E Victoria La., Fayetteville, Ark. 72701; William R. Post, 3914 Westlake Dr., Morgantown, W. Va. 26505

[21] Appl. No.: 8,499

[22] Filed: Jan. 16, 1998

Related U.S. Application Data

[60] Provisional application No. 60/035,055, Jan. 17, 1997.

[51] Int. Cl.[6] ............................................. A61F 5/00
[52] U.S. Cl. ................................. 128/882; 602/30
[58] Field of Search ..................... 602/27–29, 30; 128/882, 892

[56] References Cited

U.S. PATENT DOCUMENTS

| | | | |
|---|---|---|---|
| 1,575,042 | 3/1926 | Denniston | 602/27 |
| 4,351,324 | 9/1982 | Bronkhorst | 602/27 |
| 4,962,760 | 10/1990 | Jones | 602/27 |
| 5,282,483 | 2/1994 | Wang | 602/27 X |
| 5,329,705 | 7/1994 | Grim et al. | 602/27 X |
| 5,569,174 | 10/1996 | Varn | 602/27 |
| 5,700,237 | 12/1997 | Hess | 602/28 X |

*Primary Examiner*—Linda C.M. Dvorak
*Attorney, Agent, or Firm*—Hoffman, Wasson & Gitler

[57] ABSTRACT

The present invention is a restraint and method for stretching the plantar fascia. A foot plate in combination with a lifting member serves to elevate the phalanges and to reduce contracture of the MTP joints. Employing a leg support shell, side railings, and straps, the present invention is able to be worn at night unobstrusively but fixedly upon the lower limb. Padding throughout the present invention ensures comfort. The user can vary the angle of dorsiflexion of the phalanges by removing and attaching various lifting members to the foot plate.

18 Claims, 2 Drawing Sheets

Fig. 3
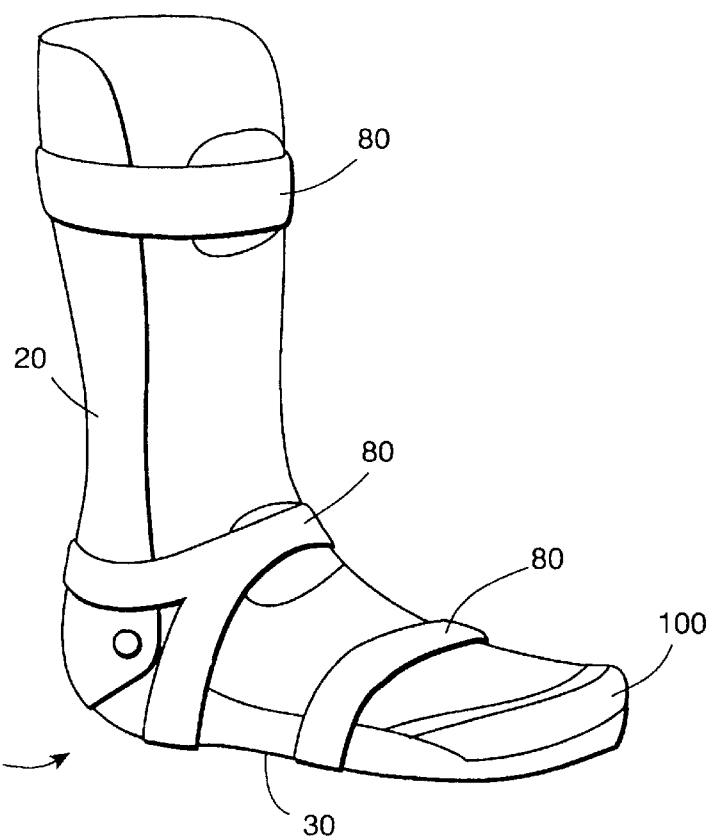
Fig. 4
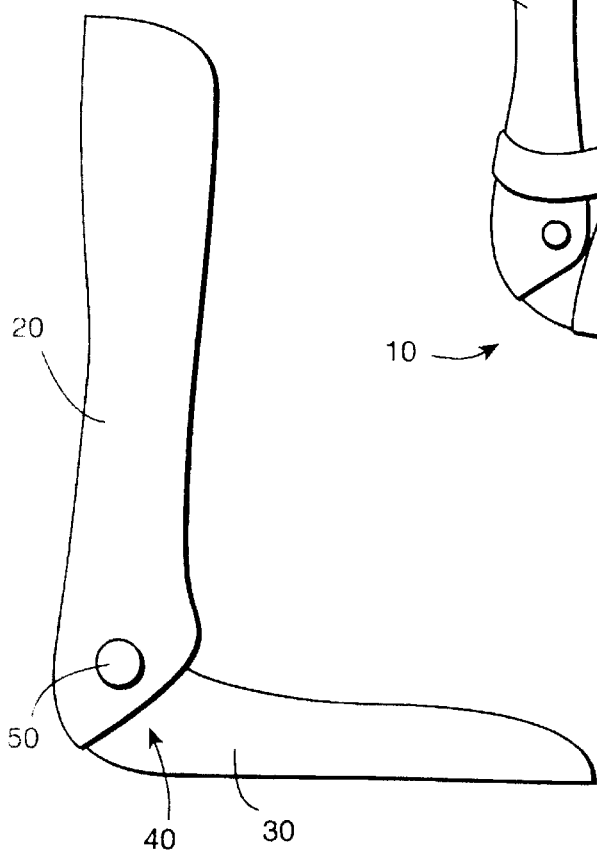
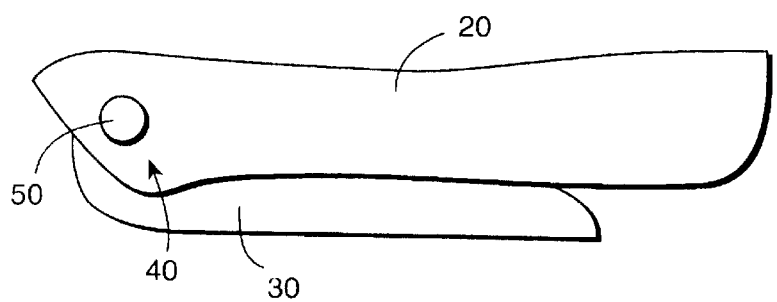
Fig. 5

RESTRAINT AND METHOD FOR THE IMPROVED TREATMENT OF RECALCITRANT PLANTAR FASCIITIS

Priority is hereby claimed to Provisional Patent Application Serial No. 60/035,055 filed on Jan. 17, 1997, in the names of Mark W. Powell and William R. Post.

FIELD OF THE INVENTION

The present invention is a restraint and method of treatment for the foot. More specifically, the present invention is a restraint and method for stretching the foot's plantar fascia.

BACKGROUND OF THE INVENTION

Recalcitrant plantar fasciitis is a common and painful condition which includes contractures of the plantar fascia and tightening of the muscles in the foot. It is characterized by chronic foot pain which frustrates both the patient and their treating physicians. The pain is typically at its worst in the morning which many professionals attribute to the fascia contractures and muscle tightening occurring at night while the individual is sleeping.

In addition, excessively pronated or supinated feet are predisposed to plantar fasciitis. Pronation of the subtalar joint everts the calcaneus and pulls the tuberosity away from the distal attachment of the plantar fascia. Excessive pronation increases the tension on the plantar fascia and its proximal attachment throughout the stance phase or gait which leads to local chronic inflammatory response.

The supinated or cavus foot has a high longitudinal arch that is rigid and less able to absorb ground reaction forces. This creates an increased demand on the plantar fascia to dissipate the resulting heightened forces exerted thereon, especially during high impact activities such as running. Plantar fasciitis can occur as unilateral involvement or bilateral involvement, where the condition occurs in one or two feet, respectively.

There are other known treatments including both surgical and nonsurgical means for relieving the symptoms of plantar fasciitis. One surgical procedure, plantar fasciotomy, also known as "open release, " has been reported to have a success rate of about 40–100%. Another surgical procedure called "endoscopic release" has a success rate of approximately 85–90%. Despite the success of these surgical methods, operative intervention is generally more costly and includes a higher risk of complication than nonsurgical treatments for the patient.

Nonsurgical treatments for plantar fasciitis have been less successful. These treatments include physical therapy, foot casting, foot taping, orthotics, heel cups, activity modification, weight loss, and medications such as non-steroidal anti-inflammatory medications and steroid injections. Occasionally, multiple treatments are prescribed for the patient. Night splints have been used, as well, to treat patients with chronic recalcitrant plantar fasciitis. However, the restraints of the prior art do not provide dorsiflexion of the phalanges at the metatarsalphalangeal (MTP) joints.

Therefore, there still exists a need for a restraint which can be easily attached and removed from a foot, but is held firmly in place when so attached to provide localized adjustable dorsiflexion of the phalanges at the MTP joints.

It is an object of the present invention to provide a rigid shell around the lower limb, ankle and foot.

It is a further object of the present invention to provide various-sized lifting members to promote dorsiflexion of the phalanges at the MTP joints.

It is another object of the present invention to provide a series of straps for easy securing and attachment of a restraint to a foot.

It is an additional object of the present invention to provide a rigid shell around the lower limb, ankle, and foot which pivots at the ankle for greater comfort.

It is a further object of the present invention to provide a rigid shell around the lower limb, ankle, and foot which folds into a compact form for storage and transportation.

It is another object of the present invention to provide a method of employing variously sized lifting members in combination with a night restraint for rehabilitation of the plantar fascia.

It also an object of the present invention to provide a restraint and method for treatment of recalcitrant plantar fasciitis which is affordable, convenient, and fully effective in accomplishing its goals.

These and other objects of the present invention will become fully apparent from the detailed description following herein.

SUMMARY OF THE INVENTION

The present invention is a foot orthotic restraint that retains the foot and phalanges in a predetermined dorsiflexion position. The present invention acts to prevent nightly contracture of the plantar fascia and thereby effectively treat plantar fasciitis.

The restraint of the present invention is a successful low risk alternative to surgery. Wearing the restraint at night alleviates the chronic pain caused by recalcitrant plantar fasciitis, especially the pain associated with the first step taken out of bed in the morning. Additionally, the present invention provides sustained improvements in alleviating the symptoms of chronic recalcitrant plantar fasciitis. In short, the present invention is a simple and effective design that is more cost effective to the patient and health care providers than the other methods of treatment.

The restraint includes a leg support shell and a foot plate adapted to hold the patient's foot. A fixed or movable lifting member is disposed on the foot plate to induce localized dorsiflexion of the phalanges at the MTP joints which results in an optimum stretching of the plantar fascia from its origin to its insertion to relieve the symptoms of plantar fasciitis. By securing the foot as such, the restraint also prevents footdrop and the accompanying muscle tightening associated therewith.

The preferred embodiment of present invention is an improved foot orthotic comprising a restraint for treating and preventing contractures of the plantar fascia and tightening of the muscles in the foot known as recalcitrant plantar fasciitis. The restraint provides dorsiflexion of the foot at the MTP joint which stretches the plantar fascia from its origin to its insertion. The plantar fascia is stretched by a lifting member positioned on the foot plate of the restraint under the phalanges such that the apex of the lifting member is at the level of the MTP joints. This position of the lifting member provides localized dorsiflexion of the MTP joints of the phalanges which results in more effective stretching of the plantar fascia. The lifting member can be adjustably positioned on the foot plate at the restraint to accommodate different foot sizes and shapes. The lifting member can be shaped however necessary to stretch the plantar fascia.

When worn at night the restraint enables the patient's foot to resist plantar-flexion induced contracture of the plantar fascia which commonly occurs during sleep thereby relieving the symptoms of recalcitrant plantar fasciitis. This then prevents sudden reinjury when the patient first steps on the ground each day, suddenly stretching the inflamed and contracted tissue. Avoidance of this cycle of reinjury relieves symptoms and facilitates healing.

The present invention has been tested in a randomized clinical trial of patients with longstanding plantar fasciitis and has proven successful in relieving symptoms. Eighty eight percent of patients treated in this study improved and maintained their improvement at completion of the study, as reported in Foot and Ankle International, 19(1):1–9, 1998, "Effective Treatment of Plantar Fasciitis with Dorsiflexion Night Splints: A Crossover Prospective Randomized Outcome Study."

BRIEF DESCRIPTION OF THE DRAWINGS

FIG. 3 is a side elevational view of the restraint of the present invention shown strapped around a lower limb and foot.

FIG. 4 is a side view of the shell of the present invention shown in an extended position.

FIG. 5 is a side view of the shell of the present invention shown in a collapsed position.

DETAILED DESCRIPTION OF THE INVENTION

Figure 1:
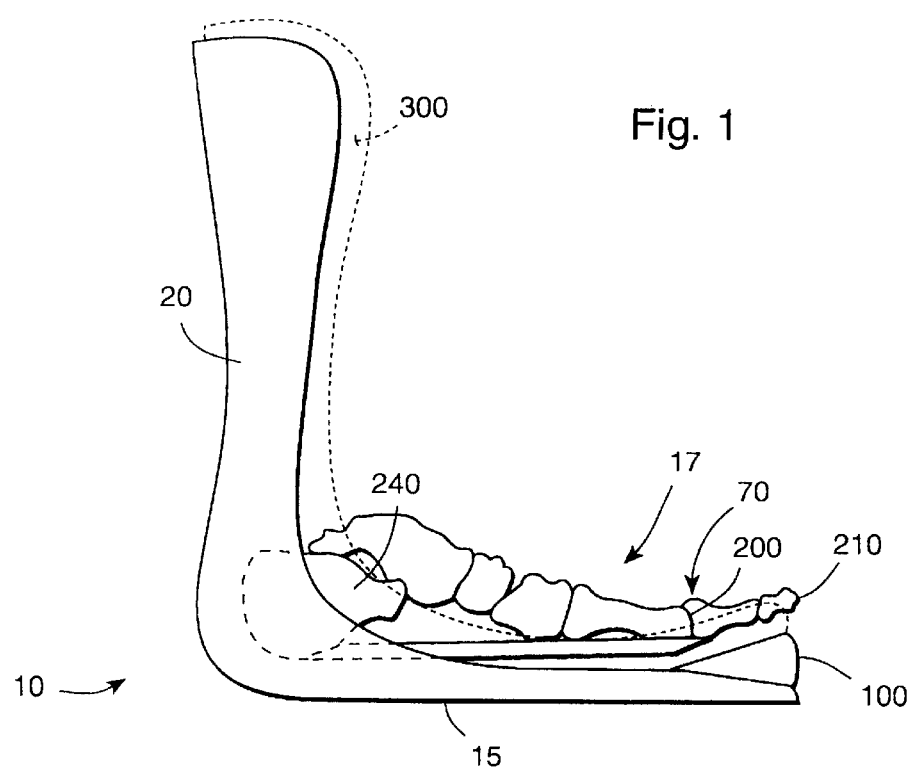
FIG. 1 is a side view of the shell and foot plate of the present disclosure, minus straps, shown in combination with the bones of a foot.

Referring to the FIGS. 1–5, the present invention will now be described. The embodiment of the restraint 10 shown in FIGS. 1–3 includes a foot plate 15 and a leg support shell 20. The foot plate 15 has a planar surface for supporting the bottom of a patient's foot 17. Side rails 30 extend upwardly from the edges of the foot plate's planar surface forming a lower profiled side railing for retaining the patient's foot 17 on the planar surface. The leg support shell 20 is generally U-shaped and extends upwardly from the foot plate 15 for engaging the lower portion of the patient's leg.

The foot plate 15 and leg support shell 20 are attached to each other by a hinge 40 as shown in the embodiment of the invention of FIGS. 4 and 5. In alternative embodiments (not shown) the foot plate 15 and leg support shell 20 are formed as one solid piece. The hinge 40 includes a male hinge portion 50 disposed on the leg support shell 20 and a female hinge portion 60 disposed on the foot plate 15. The hinge portions 50,60 snap fit together and cooperate to enable the restraint 10 to fold freely, without binding, into a collapsed position (FIG. 5) for storing an transporting and to unfold into an opened position (FIG. 4) when in use. The low side rails 30 of the foot plate 15 enable the restraint 10 to fold into a more compact profile.

The amount of dorsiflexion or the dorsiflexion angle 70 of an ankle supported in the restraint is determined by the relative position of the foot plate 15 to the leg support shell 20 when the restraint 10 is in the opened position. In the present invention, this dorsiflexion angle 70 can vary in magnitude from about 85 to 90 degrees from the plane of the foot plate, with the preferred ankle dorsiflexion angle 70 being about 95 degrees.

A plurality of straps 80 are positioned on the foot plate 15 and the leg support shell 20 to secure the restraint 10 to the patient's foot 17 and lower leg. The straps 80 include fastening strips 90, such as hook and loop type fastening elements (i.e. Velcro) and are wrapped around the patient's foot 17 and leg then fastened to hold the restraint 10 in position.

Figure 2:
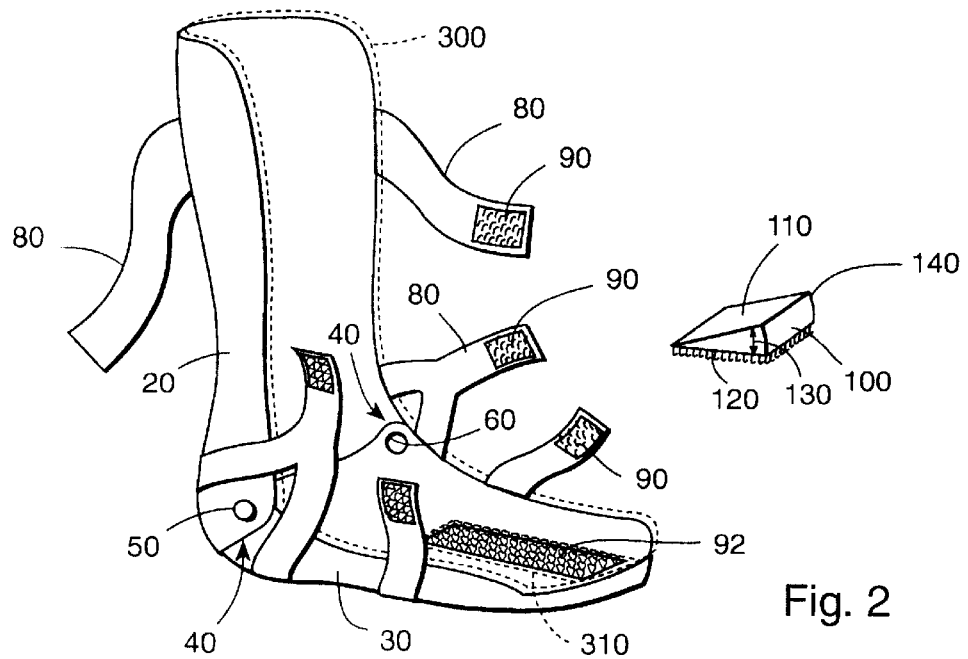
FIG. 2 is a side elevational view of the restraint of the present invention shown with the lifting member detached.

An upper surface of the foot plate 15 includes a first fastener 92, such as a hook and loop type fastening element (i.e. Velcro). The first fastener 92 is a longitudinal piece having an elongated shape, as shown in the embodiment of FIG. 2, and is generally positioned in about the middle third portion of the foot plate 15. The first fastener 92 extends from about the midsection of the foot plate 15, longitudinally, toward the distal end of the foot plate 15. It is preferable that the loop type portion of the fastening element be used as the first fastener 92 on the foot plate 15 because it is relatively softer than the hook type portion and therefore makes the restraint 10 more comfortable to wear.

The upper surface of the foot plate 15 includes a lifting member 100. In one embodiment of the present invention, the lifting member 100 has an arrow-shaped or triangular-shaped cross section. The lifting member 100 has an upper surface 110, a lower surface 120, and an included angle 130 between the upper surface 110 and the lower surface 120. A second fastener 94, such as a hook and loop type fastening element, is positioned on the lower surface 120 of the lifting member 100 to adjustably attach the lifting member 100 to the foot plate 15. The second fastener (not shown) on the lifting member 100 is complementary to the first fastener 92 on the foot plate 15 and is formed of the hook type fastening element since the cooperating loop type fastening element is preferably used to form the first fastener 92 on the foot plate 15. Consequently, the lifting member 100 can be positioned anywhere along the first fastener 92 and secured at that desired location on the foot plate 15 in order to fit the restraint 10 to a particular patient's foot 17. In an additional embodiment of the present invention (not shown), the lifting member 100 is fixed to the footplate 15. Further, another embodiment of the present invention has multiple lifting members (not shown).

A variety of lifting members 100 having different sizes and included angles 130 can be used interchangeably on the foot plate 15 during treatment. The included angles 130 range from about 10 degrees to about 30 degrees. Several different lifting members 100 may be used during the treatment of a single patient. The different sized and angled lifting members 100 can be made in different colors to enable the user to more easily identify its particular lifting member 100 of choice. Preferably, the lifting members 100 are made of foam having the necessary degree of firmness required to support the foot 17 in the maximum dorsiflexion position as required by the present invention.

The apex 140 of the lifting member 100 is positioned at the level of the MTP joints of the patient's foot 17. The first fastener 92 on the foot plate 15 and the cooperating second fastener (not shown) on the lifting member 100 enable the lifting member 100 to be positioned at different places on the foot plate 15, making the restraint 10 selectively adjustable to accommodate different foot 17 sizes and shapes. It also enables the lifting member 100 to be adjusted or "fine tuned" to the proper treatment position for an individual. The positioning of the lifting member 100 adjacent the MTP joints 200 provides localized dorsiflexion at the MTP joints 200 of the foot's phalanges 210 which results in true stretching of the plantar fascia 220 from its origin to its insertion since the terminal insertion of the plantar fascia 220 is on the proximal phalanx. The amount of dorsiflexion of the MTP joints 200 of the phalanges 210 is a function of the included angle 130 of the lifting member 100. For example, a lifting member 100 having an included angle 130 of 30 degrees would result in a localized dorsiflexion of about 30 degrees to the phalanges 210.

In one preferred embodiment of the invention as shown in FIG. 1, the restraint 10 is made from polypropylene having a 5 degree angle of dorsiflexion at the ankle 240. The lifting member 100 comprises a generally 30 degree included angle 130 with the apex 140 of the lifting member 100 positioned at the MTP joints 200 of the foot 17. So by example, the restraint 10, when worn by a patient, forces an approximate 5 degree dorsiflexion of their foot 17 at the ankle 240, while the lifting member 100 additionally forces an approximate 30 degree localized dorsiflexion of their phalanges 210 at the MTP joints 200.

When worn at night the present invention prevents plantarflexion induced contracture of the plantar fascia 220 during sleep, thereby preventing that first painful step in the morning. It is effective for treating patients having normal feet as well as supinated feet and pronated feet.

In other embodiments, padding 300 may be used to line the interior surface of the restraint 10. The padding 300 is preferably made from a soft absorbent material with an adhesive backing. The padding 300 is adhered to the upper surface of the foot plate 15. The section of padding 300 on the foot plate 15 has a cutout 310 in the middle one third of the foot plate 15 which extends around the perimeter of the first fastener 92 so that the longitudinal piece of the first fastener 92 is not covered by the padding 300. This enables the lifting member 100 to be selectively positioned along the first fastener 92 without interference from the padding 300. The foot plate 15 can be softened with further elements (not show) for extra comfort. The padding 300 can also be placed on the inner surface of the leg support shell 20, if desired. The edges of the padding 300 are generally flush with the edges of the restraint 10.

Different types of washable padding 300 can be used with the restraint. Terry cloth is an example of one type of material. Other types of padding 300 include foams that are easily washable. The thickness of the padding 300 can vary, but ¼ inch thickness is preferable.

A protective pad (not shown) can be used to cover the outside of the restraint 10. This outside protective pad (not shown) prevents the outer surface of the restraint 10 from chafing the patient's contralateral leg or other proximate limbs.

In another embodiment of the invention, as shown in FIG. 1, the foot plate 15 and the leg support shell 20 of the restraint 10 are integrally formed.

The restraint 10 can be made from a variety of materials such as polypropylene, especially any lightweight, durable plastic strong enough to secure the foot 17 in a fixed position. The restraint 10 can be made of bright colors for decorative purposes, for example, a royal blue restraint 10 with yellow or red lifting members 100 and navy blue straps 80.

To fit the restraint 10 of the present invention to a patient for treatment, a lifting member 100 of the desired included angle 130 and size is selected. The lower surface of the lifting member 100 is secured to the foot plate 15 in such a way that the apex 140 of the lifting member 100 is adjacent the patient's MTP joints 200 with the thicker end of the lifting member 100 positioned toward the free distal end of the foot plate 15. The straps 80 are then positioned around the patient's lower leg and foot 17 and fastened.

Should any transient numbness occur in the patient's phalanges 210 during treatment, the lifting member 100 should be repositioned on the foot plate 15. The lifting member 100 is selectively adjusted by removing it from the foot plate 15, moving it a small distance from its original position towards the distal end of the foot plate 15, and then reattaching it to the foot plate 15. If the numbness persists, the lifting member 100 should be readjusted at periodic intervals, until the numbness in the patient's phalanges 210 ceases.

In one preferred treatment plan using the restraint 10, the patient begins the first week wearing the restraint 10 at night and using a lifting member 100 with an included angle 130 of about 10 degrees. The included angle 130 of the lifting member 100 in the restraint 10 worn by the patient is increased by 10 degrees each week, so by the third week the patient has progressed to wearing a lifting member 100 with an included angle 130 of 30 degrees in the restraint 10.

In alternative embodiments of the present invention, the lifting member 100 can be an air bladder, a foam wedge, a plastazote, a pelite, or a gel. In various other embodiments of the present invention, the lifting member 100 can be placed within a pocket (not shown) within padding 300.

It is to be understood that the present invention is not limited to the embodiments described above, but encompasses any and all embodiments within the scope of the following claims.

What is claimed:

1. A restraint for retaining a generally planar foot in a predetermined dorsiflexion position comprising:
   a foot plate;
   a lifting member located atop said foot plate; and
   means for attaching said foot plate to an underside of a foot;
   wherein said lifting member fixedly positions toes of the foot at a greater slope than the generally planar underside of the foot.

2. The restraint of claim 1, further comprising a leg support shell attached to and extending upwardly from said foot plate, wherein said leg support shell is formed to engage a lower leg and an ankle.

3. The restraint of claim 2, wherein said leg support shell is generally U-shaped.

4. The restraint of claim 2, further comprising a means for attaching said leg support shell to said foot plate.

5. The restraint of claim 4, wherein said means for attaching said leg support to said foot plate is a hinge comprising a male portion and a female portion which interengage.

6. The restraint of claim 2, further comprising means for attaching said leg support shell to the lower leg and the ankle.

7. The restraint of claim 6, wherein said means for attaching said leg support shell to the lower leg and the ankle is at least one strap means with hook and loop fastening strips.

8. The restraint of claim 2, wherein an angle of dorsiflexion between said foot plate and said leg support shell varies from about 85 degrees to 90 degrees.

9. The restraint of claim 1, further comprising side rails attached to and extending upwardly from edges of said foot plate to form a lower profile side railing to retain the foot on said foot plate.

10. The restraint of claim 1, wherein said foot plate is planar.

11. The restraint of claim 1, wherein said means for attaching said foot plate to the foot comprises at least one strap with hook and loop fastening means positioned on said foot plate to secure said foot plate to the foot.

12. The restraint of claim 1, further comprising a first fastener element positioned atop and attached to said foot plate, said first fastener element in communication with said foot plate and said lifting member.

13. The restraint of claim 12, wherein said first fastener element includes a loop fastening element.

14. The restraint of claim 12, wherein said first fastener element is elongated, longitudinal, and positioned in about the middle third portion of said foot plate, and extending from about a midsection of said foot plate longitudinally toward a distal end of said foot plate.

15. The restraint of claim 1, wherein said lifting member has a triangular-shaped cross section.

16. The restraint of claim 1, further comprising a means for fastening said lifting member to said foot plate.

17. The restraint of claim 1, wherein a plane of said lifting member and said foot plate create an angle varying from about 0 degrees to 30 degrees.

18. The method for treatment of recalcitrant plantar fasciitis comprising the steps of:
   placing a lifting member on a foot plate;
   strapping said foot plate to a bottom of a foot; and
   varying a degree of dorsiflexion of metatarsalphalangeal joints by placing differently sized said lifting members on said foot plate;
   wherein said lifting member fixedly positions toes of the foot at a greater slope than the generally planar underside of the foot.

* * * * *